United States Patent [19]

Yamada et al.

[11] Patent Number: 5,314,819
[45] Date of Patent: May 24, 1994

[54] PROTEIN HAVING NITRILE HYDRATASE ACTIVITY OBTAINED FROM RHIZOBIUM, GENE ENCODING THE SAME, AND A METHOD FOR PRODUCING AMIDES FROM NITRILES VIA A TRANSFORMANT CONTAINING THE GENE

[75] Inventors: Kazunori Yamada, Kanagawa; Masanori Ochiai, Hokkaido; Yoshihisa Yotsumoto, Kanagawa; Yuuki Morimoto, Tokyo; Yutaka Teranishi, Kanagawa, all of Japan

[73] Assignee: Mitsubishi Kasei Corporation, Tokyo, Japan

[21] Appl. No.: 52,681

[22] Filed: Apr. 27, 1993

[30] Foreign Application Priority Data

Apr. 28, 1992 [JP] Japan .................................. 3-110244

[51] Int. Cl.$^5$ ....................... C12N 9/88; C12N 15/60; C12N 15/70
[52] U.S. Cl. .................................... 435/232; 435/69.1; 435/129; 435/71.2; 435/252.3; 435/252.33; 435/172.3; 435/320.1; 935/14; 935/29; 935/56; 935/72; 935/73; 536/23.2
[58] Field of Search ...................... 435/232, 129, 320.1, 435/69.1; 536/23.2

[56] References Cited

U.S. PATENT DOCUMENTS 5,130,235  7/1992  Beppu et al. ....................... 435/68.1

FOREIGN PATENT DOCUMENTS 444639  9/1991  European Pat. Off. .
445646  9/1991  European Pat. Off. .
502476  9/1992  European Pat. Off. .

OTHER PUBLICATIONS

Eur. J. Biochem., 181, 563–570 (1989).
J. Bacteriol., 172, 6764–6773 (1990).
J. Bacteriol., 173, 2465–2472 (1991).
J. Bacteriol., 173, 6694–6704 (1991).
Biochimica et Biophysica Acta, 1088, 225–233 (1991).
Biochimica et Biophysica Acta, 1129, 23–33 (1991).
Eur. J. Biochem., 196, 581–589 (1991).
J. Gen. Microbiol., 138, 1003–1010 (1992).

*Primary Examiner*—Robert A. Wax
*Assistant Examiner*—Rebecca Prouty
*Attorney, Agent, or Firm*—Wenderoth, Lind & Ponack

[57] ABSTRACT

A novel water-soluble enzyme protein being composed of three heterogeneous subunits and having nitrile hydratase activity was separated and purified from the bacterium of genus Rhizobium. The nucleotide sequence of the gene encoding the protein was determined; using the transformant transformed with the expression vector having the nucleotide sequence, the protein was expressed; by reacting the transformant with a nitrile in a culture broth, the corresponding amide was produced.

Via the use of a culture broth containing the transformant described above or the protein itself, a nitrile can be efficiently converted into the corresponding amide.

4 Claims, 2 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 198 amino acids
        ( B ) TYPE: amino acid
        ( C ) STRANDEDNESS: single
        ( D ) TOPOLOGY: linear (ii) MOLECULE TYPE: protein (iii) HYPOTHETICAL:

(iv) ANTI-SENSE:

(v) FRAGMENT TYPE:

(vi) ORIGINAL SOURCE:
                (A) ORGANISM: .
                (B) STRAIN: Rhizobium sp. MCI2643
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:1:

```
Met Glu Pro Tyr Thr Lys Pro Pro Ala Pro Glu Ala Leu Arg Val Lys
 1               5                  10                  15

Ala Leu Glu Thr Leu Leu Leu Glu Lys Gly Val Ile Asn Pro Gly Val
            20                  25                  30

Val Asp Ala Ile Ile Asp Val Phe Glu Asn Lys Leu Ser Pro Lys Asn
            35                  40                  45

Gly Ala Gln Val Val Ala Lys Ala Trp Thr Asp Pro Glu Phe Lys Lys
        50                  55                  60

Trp Leu Leu Glu Asp Gly Thr Ala Ala Ile Glu Ser Met Gly Phe Ser
65                  70                  75                  80

Gly Phe Gln Gly Glu Tyr Met Val Val Leu Glu Asn Thr Pro Glu Val
                85                  90                  95

His Asn Leu Val Val Cys Thr Leu Cys Ser Cys Tyr Pro Trp Pro Ile
            100                 105                 110

Leu Gly Leu Pro Pro Asn Trp Tyr Lys Thr Ala Pro Tyr Arg Ser Arg
            115                 120                 125

Ala Val Leu Asp Pro Arg Ser Val Leu Ala Glu Phe Gly Phe Asn Val
        130                 135                 140

Pro Asp Asp Val Glu Val Arg Val Trp Asp Ser Thr Ser Asp Val Arg
145                 150                 155                 160

Phe Met Val Leu Pro Met Arg Pro Asp Gly Thr Asp Gly Trp Ser Ile
                165                 170                 175
```

```
Glu Gln Leu Ala Glu Leu Val Thr Arg Asp Ser Met Ile Gly Thr Ala
            180                     185                 190

Asp Cys Lys Gln Val Val
            195
```

(2) INFORMATION FOR SEQ ID NO:2:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (iii) HYPOTHETICAL:

(iv) ANTI-SENSE:

(v) FRAGMENT TYPE:

(vi) ORIGINAL SOURCE:
        (A) ORGANISM:
        (B) STRAIN: Rhizobium sp. MCI2643
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:2:

```
Met Asn Ser Met His Asp Cys Gly Gly Leu Ala Gly Leu Gly Pro Leu
 1               5                  10                  15

Asp Ile Glu Ala Asn Glu Pro Val Phe His Glu Glu Trp Glu Gly Arg
            20                  25                  30

Met Phe Gly Ile Lys Val Asn Leu Ala Ile Glu Gly Ile Tyr Asn Ile
            35                  40                  45

Asp Glu Thr Arg Trp Ala Met Glu Gln Ile Gln Gly Leu Arg Trp Leu
        50                  55                  60

Glu Ser Ser Tyr Tyr Glu Gln Trp Ile Asp Gly Val Thr Arg Gln Met
65                  70                  75                  80

Leu Glu Lys Gly Ile Phe Thr Gln Glu Glu Leu Asp Val Arg Leu Lys
                85                  90                  95
```

Glu Leu Ala Glu Gln Glu Gly Thr
               100

( 2 ) INFORMATION FOR SEQ ID NO:3:

( i ) SEQUENCE CHARACTERISTICS:
        ( A ) LENGTH: 115 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN: Rhizobium sp. MCI2643
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:3:

Ala Gly Val Asn Pro Glu Asp Ile Pro Gly Ile Ile Ala Thr Asn Phe
 1               5                  10                 15

Ser Pro Met Ala Glu Val Asp Thr Pro Pro Arg Phe Lys Val Gly Asp
              20                 25                 30

Lys Val Arg Ala Val Ile Asp Ala Lys Pro Thr His Thr Arg Leu Pro
             35                 40                 45

Arg Tyr Leu Arg Gly Arg Val Gly Thr Ile Val Lys His Tyr Gly Gly
         50                 55                 60

Met Val Phe Ala Asp Thr Arg Ala Leu Lys Gln Gly Asp Asn Pro Gln
 65                 70                 75                 80

His Ile Tyr Ser Val Arg Phe Glu Gly Ala Asp Val Trp Gly Lys Glu
             85                 90                 95

Thr Gly Gly Asn Asn Thr Phe Tyr Ala Asp Met Tyr Glu Ser Tyr Ile
            100                105                110

Glu Asn Gln
         115

(2) INFORMATION FOR SEQ ID NO:4:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (iii) HYPOTHETICAL:

(iv) ANTI-SENSE:

(v) FRAGMENT TYPE:

(vi) ORIGINAL SOURCE:
        (A) ORGANISM:
        (B) STRAIN: Rhizobium sp. MCI2643
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:4:

```
Met Ala Gly Val Asn Pro Glu Asp Ile Pro Gly Ile Ile Ala Thr Asn
 1               5                  10                  15

Phe Ser Pro Met Ala Glu Val Asp Thr Pro Pro Arg Phe Lys Val Gly
                20                  25                  30

Asp Lys Val Arg Ala Val Ile Asp Ala Lys Pro Thr His Thr Arg Leu
            35                  40                  45

Pro Arg Tyr Leu Arg Gly Arg Val Gly Thr Ile Val Lys His Tyr Gly
        50                  55                  60

Gly Met Val Phe Ala Asp Thr Arg Ala Leu Lys Gln Gly Asp Asn Pro
65                  70                  75                  80

Gln His Ile Tyr Ser Val Arg Phe Glu Gly Ala Asp Val Trp Gly Lys
                85                  90                  95

Glu Thr Gly Gly Asn Asn Thr Phe Tyr Ala Asp Met Tyr Glu Ser Tyr
                100                 105                 110
```

Ile Glu Asn Gln
          115

( 2 ) INFORMATION FOR SEQ ID NO:5:

( i ) SEQUENCE CHARACTERISTICS:
        ( A ) LENGTH: 966 base pairs
        ( B ) TYPE: nucleic acid
        ( C ) STRANDEDNESS: double
        ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN: Rhizobium sp. MCI2643
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE: J121

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: P CDS( subunit)
        ( B ) LOCATION: 1..597
        ( C ) IDENTIFICATION METHOD: E
        ( D ) OTHER INFORMATION:

( i x ) FEATURE:
        ( A ) NAME/KEY: P CDS( subunit)
        ( B ) LOCATION: 627..941
        ( C ) IDENTIFICATION METHOD: E
        ( D ) OTHER INFORMATION:

( i x ) FEATURE:
        ( A ) NAME/KEY: P CDS(N-terminal sequence of subunit)
        ( B ) LOCATION: 941..966
        ( C ) IDENTIFICATION METHOD: E
        ( D ) OTHER INFORMATION:

( i x ) FEATURE:
        ( A ) NAME/KEY:
        ( B ) LOCATION:
        ( C ) IDENTIFICATION METHOD:
        ( D ) OTHER INFORMATION: /note ="N is A or G or C or T"

( i x ) FEATURE:
        ( A ) NAME/KEY:
        ( B ) LOCATION:
        ( C ) IDENTIFICATION METHOD:
        ( D ) OTHER INFORMATION: /note ="R is A or G"

( i x ) FEATURE:
        ( A ) NAME/KEY:
        ( B ) LOCATION:
        ( C ) IDENTIFICATION METHOD:
        ( D ) OTHER INFORMATION: /note ="Y is C or T"

( x ) PUBLICATION INFORMATION:
        ( A ) AUTHORS:
        ( B ) TITLE:
        ( C ) JOURNAL:
        ( D ) VOLUME:

-continued (E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:5:

| ATG | GAR | CCN | TAY | ACN | AAR | CCG | CCG | GCA | CCC | GAA | GCG | CTG | CGC | GTC | AAA | 48 |
| Met | Glu | Pro | Tyr | Thr | Lys | Pro | Pro | Ala | Pro | Glu | Ala | Leu | Arg | Val | Lys | |
| 1 | | | | 5 | | | | | 10 | | | | | 15 | | |

| GCG | CTG | GAA | ACA | CTG | CTG | CTG | GAA | AAA | GGC | GTC | ATA | AAC | CCG | GGT | GTT | 96 |
| Ala | Leu | Glu | Thr | Leu | Leu | Leu | Glu | Lys | Gly | Val | Ile | Asn | Pro | Gly | Val | |
| | | | 20 | | | | | 25 | | | | | 30 | | | |

| GTC | GAC | GCG | ATT | ATC | GAT | GTA | TTC | GAA | AAC | AAG | CTT | AGT | CCG | AAG | AAC | 144 |
| Val | Asp | Ala | Ile | Ile | Asp | Val | Phe | Glu | Asn | Lys | Leu | Ser | Pro | Lys | Asn | |
| | | 35 | | | | | 40 | | | | | 45 | | | | |

| GGC | GCT | CAG | GTT | GTT | GCG | AAA | GCC | TGG | ACA | GAC | CCT | GAG | TTC | AAA | AAA | 192 |
| Gly | Ala | Gln | Val | Val | Ala | Lys | Ala | Trp | Thr | Asp | Pro | Glu | Phe | Lys | Lys | |
| | 50 | | | | | 55 | | | | | 60 | | | | | |

| TGG | CTC | TTG | GAA | GAC | GGC | ACA | GCA | GCA | ATT | GAA | TCG | ATG | GGC | TTT | AGT | 240 |
| Trp | Leu | Leu | Glu | Asp | Gly | Thr | Ala | Ala | Ile | Glu | Ser | Met | Gly | Phe | Ser | |
| 65 | | | | | 70 | | | | | 75 | | | | | 80 | |

| GGC | TTT | CAG | GGC | GAA | TAC | ATG | GTC | GTT | CTG | GAG | AAC | ACG | CCA | GAG | GTG | 288 |
| Gly | Phe | Gln | Gly | Glu | Tyr | Met | Val | Val | Leu | Glu | Asn | Thr | Pro | Glu | Val | |
| | | | | 85 | | | | | 90 | | | | | 95 | | |

| CAT | AAC | CTT | GTC | GTT | TGC | ACG | CTG | TGT | TCG | TGC | TAC | CCG | TGG | CCG | ATA | 336 |
| His | Asn | Leu | Val | Val | Cys | Thr | Leu | Cys | Ser | Cys | Tyr | Pro | Trp | Pro | Ile | |
| | | | 100 | | | | | 105 | | | | | 110 | | | |

| CTG | GGG | TTG | CCG | CCT | AAT | TGG | TAT | AAA | ACA | GCC | CCT | TAC | CGT | AGC | CGT | 384 |
| Leu | Gly | Leu | Pro | Pro | Asn | Trp | Tyr | Lys | Thr | Ala | Pro | Tyr | Arg | Ser | Arg | |
| | | 115 | | | | | 120 | | | | | 125 | | | | |

| GCA | GTT | CTG | GAT | CCG | CGT | TCT | GTT | TTG | GCA | GAA | TTC | GGT | TTC | AAC | GTG | 432 |
| Ala | Val | Leu | Asp | Pro | Arg | Ser | Val | Leu | Ala | Glu | Phe | Gly | Phe | Asn | Val | |
| | 130 | | | | | 135 | | | | | 140 | | | | | |

| CCA | GAT | GAT | GTT | GAA | GTC | CGG | GTC | TGG | GAT | TCT | ACC | TCC | GAC | GTT | CGT | 480 |
| Pro | Asp | Asp | Val | Glu | Val | Arg | Val | Trp | Asp | Ser | Thr | Ser | Asp | Val | Arg | |
| 145 | | | | | 150 | | | | | 155 | | | | | 160 | |

| TTC | ATG | GTT | CTG | CCA | ATG | CGA | CCC | GAT | GGC | ACT | GAT | GGC | TGG | AGC | ATA | 528 |
| Phe | Met | Val | Leu | Pro | Met | Arg | Pro | Asp | Gly | Thr | Asp | Gly | Trp | Ser | Ile | |
| | | | | 165 | | | | | 170 | | | | | 175 | | |

| GAA | CAG | CTA | GCA | GAA | CTG | GTC | ACC | CGA | GAC | TCA | ATG | ATC | GGC | ACT | GCC | 576 |
| Glu | Gln | Leu | Ala | Glu | Leu | Val | Thr | Arg | Asp | Ser | Met | Ile | Gly | Thr | Ala | |
| | | | 180 | | | | | 185 | | | | | 190 | | | |

| GAT | TGC | AAA | CAA | GTC | GTC | TGAGCA | GCAAACGCAA | CTCGCAGGAG | GAAATT | ATG | 629 |
| Asp | Cys | Lys | Gln | Val | Val | | | | | Met | |
| | | 195 | | | | | | | | | |

| AAC | TCG | ATG | CAT | GAC | TGT | GGC | GGT | CTG | GCT | GGT | CTT | GGC | CCG | CTC | GAC | 677 |
| Asn | Ser | Met | His | Asp | Cys | Gly | Gly | Leu | Ala | Gly | Leu | Gly | Pro | Leu | Asp | |
| 200 | | | | | 205 | | | | | 210 | | | | | 215 | |

| ATC | GAA | GCG | AAC | GAA | CCT | GTG | TTT | CAC | GAG | GAG | TGG | GAA | GGC | CGG | ATG | 725 |
| Ile | Glu | Ala | Asn | Glu | Pro | Val | Phe | His | Glu | Glu | Trp | Glu | Gly | Arg | Met | |
| | | | | 220 | | | | | 225 | | | | | 230 | | |

| TTC | GGC | ATC | AAG | GTG | AAT | CTG | GCG | ATT | GAG | GGC | ATC | TAT | AAT | ATT | GAC | 733 |
| Phe | Gly | Ile | Lys | Val | Asn | Leu | Ala | Ile | Glu | Gly | Ile | Tyr | Asn | Ile | Asp | |
| | | | 235 | | | | | 240 | | | | | 245 | | | |

| GAG | ACC | CGC | TGG | GCG | ATG | GAG | CAA | ATA | CAA | GGC | CTG | CGC | TGG | TTG | GAA | 821 |
| Glu | Thr | Arg | Trp | Ala | Met | Glu | Gln | Ile | Gln | Gly | Leu | Arg | Trp | Leu | Glu | |
| | | 250 | | | | | 255 | | | | | 260 | | | | |

| TCC | AGC | TAT | TAC | GAA | CAA | TGG | ATT | GAC | GGA | GTT | ACT | CGT | CAA | ATG | TTG | 869 |
| Ser | Ser | Tyr | Tyr | Glu | Gln | Trp | Ile | Asp | Gly | Val | Thr | Arg | Gln | Met | Leu | |
| | 265 | | | | | 270 | | | | | 275 | | | | | |

| | | | | | | | | | | | | | | |
|---|---|---|---|---|---|---|---|---|---|---|---|---|---|---|
|GAA|AAG|GGC|ATC|TTC|ACT|CAA|GAA|GAG|CTT|GAT|GTC|CGC|CTC|AAG|GAA 917|
|Glu|Lys|Gly|Ile|Phe|Thr|Gln|Glu|Glu|Leu|Asp|Val|Arg|Leu|Lys|Glu|
|280| | | | |285| | | |290| | | | |295| |

| | | | | | | | | | | | | | |
|---|---|---|---|---|---|---|---|---|---|---|---|---|---|
|CTT|GCA|GAG|CAG|GAG|GGC|ACG|TG ATG|GCT|GGN|GTN|AAY|CCN|GAR GAY AT 966|
|Leu|Ala|Glu|Gln|Glu|Gly|Thr|Met|Ala|Gly|Val|Asn|Pro|Glu Asp|
| | | | |300| | | |305| | | | |310|

( 2 ) INFORMATION FOR SEQ ID NO:6:

( i ) SEQUENCE CHARACTERISTICS:
    ( A ) LENGTH: 1291 base pairs
    ( B ) TYPE: nucleic acid
    ( C ) STRANDEDNESS: double
    ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN: Rhizobium sp. MCI2643
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE: pChAM24-1

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY: P CDS( subunit)
    ( B ) LOCATION: 1..597
    ( C ) IDENTIFICATION METHOD: E
    ( D ) OTHER INFORMATION:

( i x ) FEATURE:
    ( A ) NAME/KEY: P CDS( subunit)
    ( B ) LOCATION: 627..941
    ( C ) IDENTIFICATION METHOD: E
    ( D ) OTHER INFORMATION:

( i x ) FEATURE:
    ( A ) NAME/KEY: P CDS( subunit)
    ( B ) LOCATION: 941..1291
    ( C ) IDENTIFICATION METHOD: E
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:6:

ATGGAACCAT ATACCAAACC GCCGGCACCC GAAGCGCTGC GCGTCAAAGC GCTGGAAACA    60

CTGCTGCTGG AAAAAGGCGT CATAAACCCG GGTGTTGTCG ACGCGATTAT CGATGTATTC   120

| | | | | | | |
|---|---|---|---|---|---|---|
| GAAAACAAGC | TTAGTCCGAA | GAACGGCGCT | CAGGTTGTTG | CGAAAGCCTG | GACAGACCCT | 180 |
| GAGTTCAAAA | AATGGCTCTT | GGAAGACGGC | ACAGCAGCAA | TTGAATCGAT | GGGCTTTAGT | 240 |
| GGCTTTCAGG | GCGAATACAT | GGTCGTTCTG | GAGAACACGC | CAGAGGTGCA | TAACCTTGTC | 300 |
| GTTTGCACGC | TGTGTTCGTG | CTACCCGTGG | CCGATACTGG | GGTTGCCGCC | TAATTGGTAT | 360 |
| AAAACAGCCC | CTTACCGTAG | CCGTGCAGTT | CTGGATCCGC | GTTCTGTTTT | GGCAGAATTC | 420 |
| GGTTTCAACG | TGCCAGATGA | TGTTGAAGTC | CGGGTCTGGG | ATTCTACCTC | CGACGTTCGT | 480 |
| TTCATGGTTC | TGCCAATGCG | ACCCGATGGC | ACTGATGGCT | GGAGCATAGA | ACAGCTAGCA | 540 |
| GAACTGGTCA | CCCGAGACTC | AATGATCGGC | ACTGCCGATT | GCAAACAAGT | CGTCTGAGCA | 600 |
| GCAAACGCAA | CTCGCAGGAG | GAAATTATGA | ACTCGATGCA | TGACTGTGGC | GGTCTGGCTG | 660 |
| GTCTTGGCCC | GCTCGACATC | GAAGCGAACG | AACCTGTGTT | TCACGAGGAG | TGGGAAGGCC | 720 |
| GGATGTTCGG | CATCAAGGTG | AATCTGGCGA | TTGAGGGCAT | CTATAATATT | GACGAGACCC | 780 |
| GCTGGGCGAT | GGAGCAAATA | CAAGGCCTGC | GCTGGTTGGA | ATCCAGCTAT | TACGAACAAT | 840 |
| GGATTGACGG | AGTTACTCGT | CAAATGTTGG | AAAAGGGCAT | CTTCACTCAA | GAAGAGCTTG | 900 |
| ATGTCCGCCT | CAAGGAACTT | GCAGAGCAGG | AGGGCACGTG | ATGGCTGGAG | TTAACCCTGA | 960 |
| AGATATTCCT | GGGATTATCG | CTACAAATTT | TTCGCCGATG | GCTGAAGTCG | ATACGCCGCC | 1020 |
| GAGGTTCAAA | GTCGGCGACA | AGGTGCGCGC | TGTTATAGAC | GCAAAACCAA | CTCATACACG | 1080 |
| ACTGCCGCGC | TATCTACGTG | GGCGCGTCGG | TACCATAGTG | AAGCACTACG | GCGGTATGGT | 1140 |
| ATTCGCCGAT | ACCCGTGCTC | TCAAGCAAGG | CGACAATCCT | CAGCATATCT | ATTCAGTCCG | 1200 |
| ATTTGAGGGT | GCTGATGTTT | GGGGCAAGGA | AACAGGCGGC | AACAATACAT | TCTACGCGGA | 1260 |
| CATGTATGAA | AGCTACATAG | AAAACCAATG | A | | | 1291 |

( 2 ) INFORMATION FOR SEQ ID NO:7:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: syntheic DNA ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION: /note="R is G or A"

( i x ) FEATURE:
  ( A ) NAME/KEY:
  ( B ) LOCATION:
  ( C ) IDENTIFICATION METHOD:
  ( D ) OTHER INFORMATION: /note="N is inosine"

( i x ) FEATURE:
  ( A ) NAME/KEY:
  ( B ) LOCATION:
  ( C ) IDENTIFICATION METHOD:
  ( D ) OTHER INFORMATION: /note="Y is C or T"

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:
  ( K ) RELEVANT RESIDUES IN SEQ ID NO:

( x i ) SEQUENCE DESCRIPTION: SEQ ID NO:7:

ATGGARCCNT AYACNAARCC      20

( 2 ) INFORMATION FOR SEQ ID NO:8:

( i ) SEQUENCE CHARACTERISTICS:
  ( A ) LENGTH: 20 bases
  ( B ) TYPE: nucleic acid
  ( C ) STRANDEDNESS: single
  ( D ) TOPOLOGY: linear ( i i ) MOLECULE TYPE: syntheic DNA ( i i i ) HYPOTHETICAL:

( i v ) ANTI-SENSE:

( v ) FRAGMENT TYPE:

( v i ) ORIGINAL SOURCE:
  ( A ) ORGANISM:
  ( B ) STRAIN:
  ( C ) INDIVIDUAL ISOLATE:
  ( D ) DEVELOPMENTAL STAGE:
  ( E ) HAPLOTYPE:
  ( F ) TISSUE TYPE:
  ( G ) CELL TYPE:
  ( H ) CELL LINE:
  ( I ) ORGANELLE:

( v i i ) IMMEDIATE SOURCE:
  ( A ) LIBRARY:
  ( B ) CLONE:

( v i i i ) POSITION IN GENOME:
  ( A ) CHROMOSOME/SEGMENT:
  ( B ) MAP POSITION:
  ( C ) UNITS:

( i x ) FEATURE:
  ( A ) NAME/KEY:
  ( B ) LOCATION:
  ( C ) IDENTIFICATION METHOD:
  ( D ) OTHER INFORMATION: /note="R is G or A"

( i x ) FEATURE:
  ( A ) NAME/KEY:
  ( B ) LOCATION:
  ( C ) IDENTIFICATION METHOD:
  ( D ) OTHER INFORMATION: /note="N is inosine"

( i x ) FEATURE:
  ( A ) NAME/KEY:
  ( B ) LOCATION:

( C ) IDENTIFICATION METHOD:
( D ) OTHER INFORMATION: /note="Y is C or T"

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:8:

ATRTCYTCNG GRTTNACNCC         20

( 2 ) INFORMATION FOR SEQ ID NO:9:

( i ) SEQUENCE CHARACTERISTICS:
( A ) LENGTH: 40 amino acids
( B ) TYPE: amino acid
( C ) STRANDEDNESS: single
( D ) TOPOLOGY: linear ( i i ) MOLECULE TYPE: peptide ( i i i ) HYPOTHETICAL:

( i v ) ANTI-SENSE:

( v ) FRAGMENT TYPE: N-terminal fragment ( v i ) ORIGINAL SOURCE:
( A ) ORGANISM:
( B ) STRAIN: Rhizobium sp. MCI2643
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY:
( B ) LOCATION:
( C ) IDENTIFICATION METHOD:
( D ) OTHER INFORMATION: /note="Xaa is unknown"

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:9:

Met Glu Pro Tyr Thr Lys Pro Pro Ala Cys Glu Ala Leu Arg Val Lys
 1               5                  10                  15

Ala Leu Glu Thr Xaa Leu Leu Glu Lys Gly Val Ile Asn Val Gly Xaa

```
                     20                    25                  30
Xaa Xaa Ala Ile Ile Asp Xaa Phe
             35                   40
```

(2) INFORMATION FOR SEQ ID NO:10:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (iii) HYPOTHETICAL:

(iv) ANTI-SENSE:

(v) FRAGMENT TYPE: N-terminal fragment (vi) ORIGINAL SOURCE:
        (A) ORGANISM:
        (B) STRAIN: Rhizobium sp. MCI2643
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:10:

```
Met Asn Ser Met His Asp Thr Gly Gly Leu Ala Gly Pro Leu Asp Ile
 1               5                  10                  15

Glu Ala Asn Glu Pro Val Phe His Glu Glu Trp Glu
                20              25
```

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL:

( i v ) ANTI-SENSE:

( v ) FRAGMENT TYPE: N-terminal fragment ( v i ) ORIGINAL SOURCE:
  ( A ) ORGANISM:
  ( B ) STRAIN: Rhizobium sp. MCI2643
  ( C ) INDIVIDUAL ISOLATE:
  ( D ) DEVELOPMENTAL STAGE:
  ( E ) HAPLOTYPE:
  ( F ) TISSUE TYPE:
  ( G ) CELL TYPE:
  ( H ) CELL LINE:
  ( I ) ORGANELLE:

( v i i ) IMMEDIATE SOURCE:
  ( A ) LIBRARY:
  ( B ) CLONE:

( v i i i ) POSITION IN GENOME:
  ( A ) CHROMOSOME/SEGMENT:
  ( B ) MAP POSITION:
  ( C ) UNITS:

( i x ) FEATURE:
  ( A ) NAME/KEY:
  ( B ) LOCATION:
  ( C ) IDENTIFICATION METHOD:
  ( D ) OTHER INFORMATION:

( x ) PUBLICATION INFORMATION:
  ( A ) AUTHORS:
  ( B ) TITLE:
  ( C ) JOURNAL:
  ( D ) VOLUME:
  ( E ) ISSUE:
  ( F ) PAGES:
  ( G ) DATE:
  ( H ) DOCUMENT NUMBER:
  ( I ) FILING DATE:
  ( J ) PUBLICATION DATE:
  ( K ) RELEVANT RESIDUES IN SEQ ID NO:

( x i ) SEQUENCE DESCRIPTION: SEQ ID NO:11:

```
Gly Ile Phe Thr Gln Glu Glu Leu Asp Val Arg Leu Lys
 1               5                   10
```

( 2 ) INFORMATION FOR SEQ ID NO:12:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL:

( i v ) ANTI-SENSE:

( v ) FRAGMENT TYPE: N-terminal fragment ( v i ) ORIGINAL SOURCE:
    ( A ) ORGANISM:
    ( B ) STRAIN: Rhizobium sp. MCI2643
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:

(B) MAP POSITION:
(C) UNITS:

(ix) FEATURE:
  (A) NAME/KEY:
  (B) LOCATION:
  (C) IDENTIFICATION METHOD:
  (D) OTHER INFORMATION:

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (H) DOCUMENT NUMBER:
  (I) FILING DATE:
  (J) PUBLICATION DATE:
  (K) RELEVANT RESIDUES IN SEQ ID NO:

(xi) SEQUENCE DESCRIPTION: SEQ ID NO:12:

```
Ala Gly Val Asn Pro Glu Asp Ile Pro Gly Ile Ile Ala Thr Asn Phe
 1           5                  10                  15
Ser Pro Met Ala
         20
```

(2) INFORMATION FOR SEQ ID NO:13:

(i) SEQUENCE CHARACTERISTICS:
    (A) LENGTH: 17 bases
    (B) TYPE: nucleic acid
    (C) STRANDEDNESS: single
    (D) TOPOLOGY: linear (ii) MOLECULE TYPE: synthetic DNA (iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:

```
        (I) FILING DATE:
        (J) PUBLICATION DATE:
        (K) RELEVANT RESIDUES IN SEQ ID NO:

(xi) SEQUENCE DESCRIPTION: SEQ ID NO:13:

GTAAAACGAC GGCCAGT          17

(2) INFORMATION FOR SEQ ID NO:14:

(i) SEQUENCE CHARACTERISTICS:
        (A) LENGTH: 17 bases
        (B) TYPE: nucleic acid
        (C) STRANDEDNESS: single
        (D) TOPOLOGY: linear (ii) MOLECULE TYPE: synthetic DNA (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:14:

CAGGAAACAG CTATGAC          17
```

PROTEIN HAVING NITRILE HYDRATASE ACTIVITY OBTAINED FROM RHIZOBIUM, GENE ENCODING THE SAME, AND A METHOD FOR PRODUCING AMIDES FROM NITRILES VIA A TRANSFORMANT CONTAINING THE GENE

BACKGROUND OF THE INVENTION

The present invention relates to a novel protein having nitrile hydratase activity, the gene encoding the same, and a method for producing an amide from a nitrile via a transformant containing the gene. More specifically, the present invention relates to a novel protein having the activity of generating from a nitrile the corresponding amide; the gene encoding the same; a transformant transformed with an expression vector having a promoter sequence required at least for the expression of the protein; the DNA sequence encoding the protein and a terminator sequence; a method for expressing the protein via the culture of the transformant; a method for producing an amide by treating a nitrile with a culture broth containing the transformant or protein itself; an isolated microorganism; a treated microorganism; and protein or the immobilized products thereof.

For the technique to convert the nitrile groups of nitriles into amide groups by hydration, thereby producing the corresponding amides, there have been known a heating process using an acid or an alkali as a reaction catalyst and a heating process using copper catalysts. In recent years, however, a method has been adopted using a bacterial catalyst containing a water-soluble enzyme protein, namely nitrile hydratase, catalyzing the hydration reaction, (see Japanese Patent Applications Laid-open Publication Nos. 2693/1984 and 86889/1989; European Patent Applications Publication Nos. 188,316, 204,555, 444,639, and 93,782; U.S. Pat. Nos. 5,130,235 and 4,001,081; U.K. Patent Applications Publication Nos. 2,018,240, 2,076,820, and 2,076,821). It is believed that the method using the bacterial catalyst is superior to other methods, in that the hydration reaction can be carried out at ambient temperature and a higher conversion ratio can be achieved according to the method.

In using a bacterial catalyst, however, numerous considerations are required in preparing the bacterial catalyst, depending on the biological features of the bacterial catalyst to be used, such as the safety assessment of the bacterium, the optimum culture condition, and the like. Therefore, the activity as a biological catalyst is not necessarily readily increased to a level industrially applicable from the respect of cost.

As a method for improving such bacterial catalyst processes, a process is under investigation, comprising preparing a bacterial catalyst, namely an enzyme nitrile hydratase per se, via genetic engineering and converting nitriles into the corresponding amides. For example, Japanese Patent Application Laid-open No. 137688/1988 describes at an enzyme level a type of nitrile hydratase composed of two heterogeneous subunits and derived from genus Rhodococcus; Japanese Patent Application Laid-open No. 119778/1990 discloses a nitrile hydratase gene composed of two heterogeneous subunits and derived from genus Rhodococcus; and European Patent Application Publication No. 444,639 discloses a nitrile hydratase gene composed of two heterogeneous subunits and derived from genus Pseudomonas; and European Patent application Publication No. 455,646 discloses a nitrile hydratase gene composed of two heterogeneous subunits and derived from *Rhodococcus rhodochrous*.

For the purpose of preparing a bacterial catalyst with a higher catalytic activity, the present inventors have made investigations so as to produce a large quantity of a protein having an extremely high hydration activity of nitriles, namely nitrile hydratase activity, in a transformant via recombinant DNA technology. Consequently, the inventors have isolated and purified for the first time a novel protein useful for such an objective (often referred to as "nitrile hydratase protein", "nitrile hydratase AM24 protein", or "AM 24 protein" hereinbelow). Furthermore, the present inventors have separated and isolated the gene encoding the protein. Additionally, they have integrated the gene into an expression vector to generate a transformant, and have successfully achieved the large scale production of the nitrile hydratase protein via the transformant. Thus, the inventors have accomplished the present invention.

SUMMARY OF THE INVENTION

The summary of the present invention resides in a novel protein having the following characteristic physicochemical properties; the gene encoding the protein, and a method for preparing amides from nitriles via the transformant containing the gene:

1. A water-soluble enzyme protein composed of three types of subunits and having a molecular weight of about 110,000 determined by gel filtration, wherein the molecular weights of the individual subunits determined by SDS polyacrylamide gel electrophoresis are as follows;

molecular weight of subunit $\alpha$; 26,000±500 Dalton
molecular weight of subunit $\beta$; 15,000±500 Dalton
molecular weight of subunit $\gamma$; 16,500±500 Dalton 2. Having nitrile hydratase activity.

The present invention will now be explained in detail.

BRIEF DESCRIPTION OF THE DRAWING

In the accompanying drawings.

In the figure, $Amp^r$ represents ampicillin resistant gene; COS represents COS region; and ori represents a replication initiation site.

Figure 2:
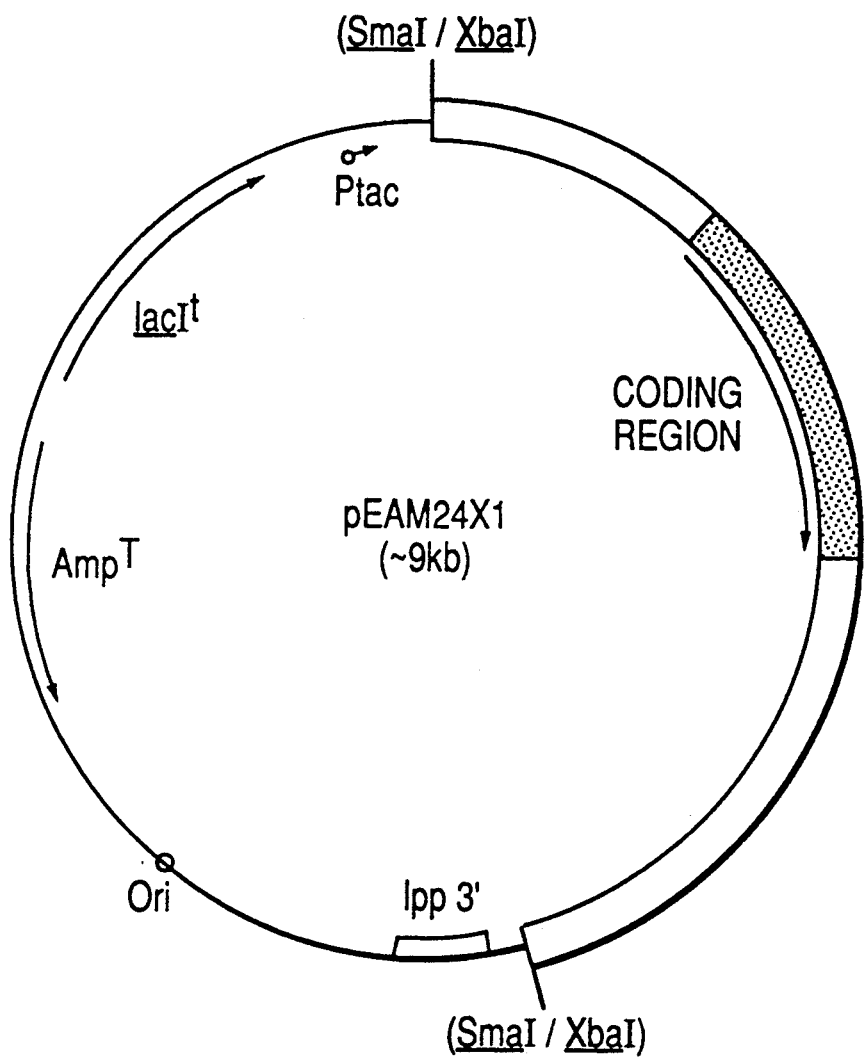

FIG. 2 shows the construction of the vector pEAM24X1 expressing the AM24 protein of the present invention.

Figure 1:
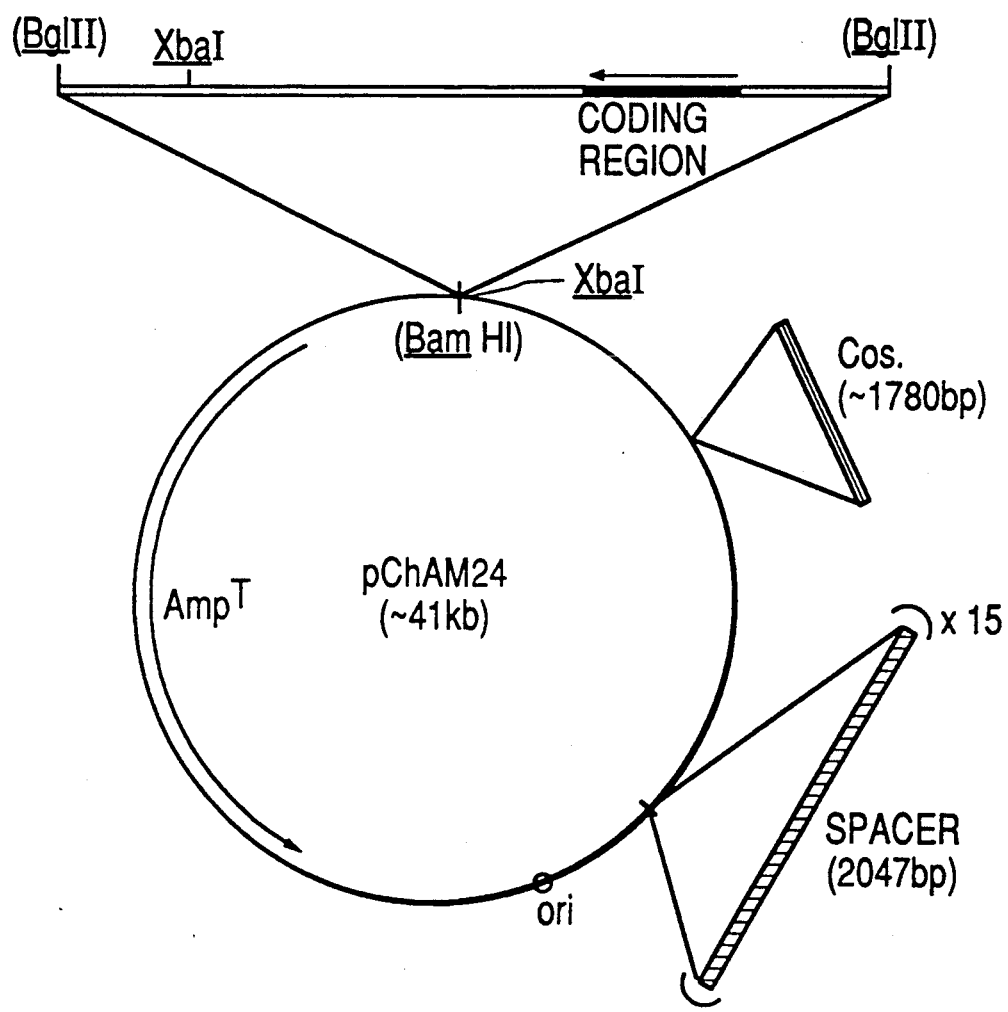
FIG. 1 shows the constructions of a Charomide clone, pChAM24-1, having a DNA fragment including a region of the gene encoding the AM24 protein of the present invention, and an AM24 protein expression vector, pEAM24X1.

In the figure, $Amp^r$ and ori are the same as in FIG. 1; lacIq represents repressor gene; $P_{tac}$ represents tac promoter; and lpp3' represents lpp gene terminator region.

DETAILED DESCRIPTION OF THE PREFERRED EMBODIMENTS

The novel protein, nitrile hydratase AM24 protein, of the present invention can be purified as follows. As will be described in the working examples hereinbelow, the bacterium Rhizobium sp. MCI2643 (European Patent Application No. 92,113,339.3; FERM BP-3953 as the deposition number in the Patent Microorganism Depository, Fermentation Institute, Agency of Industrial Science and Technology at 1-3, Higashi 1-chome, Tsukuba-shi, Ibaraki-ken, 305, Japan) is disrupted and centrifuged, and the resulting supernatant is fractionated by hydrophobic chromatography on a Butyl-Toyopearl column (manufactured by TOSOH Corporation), etc. The desired peak is then further fractionated by chromatography on a DEAE-Toyopearl column and the like. The fraction is finally subjected to molecular sieve chromatography with TSK gel G3000SW and the like, thereby yielding a purified sample. The purified protein of the present invention is a water-soluble protein composed of three subunits, α, β and γ subunits, having molecuar weights of 26,000±500 Dalton, 15,000±500 Dalton, and 16,500±500 Dalton, respectively, determined by SDS-polacrylamide electrophoresis, and having an activity to convert nitriles into amides via hydration reaction, namely nitrile hydratase activity.

The AM24 protein of the present invention is a protein composed of three subunits having amino acid sequences shown in SEQ ID Nos. 1, 2, 3, and 4, namely α-subunit (SEQ ID No. 1), β-subunit (SEQ ID No. 2) and γ subunit (SEQ ID No. 3 or 4). Broadly modified products thereof, such as those produced after the removal, substitution, modification or addition of a part of the amino acids, are also included within the AM24 protein of the present invention.

The gene encoding the AM24 protein includes, for example, those having a nucleotide sequence shown in SEQ ID No. 5 or 6.

The DNA fragment of the gene encoding the AM24 protein of the present invention can be generated, for example, by the following process.

As a DNA library containing the gene encoding the protein of the present invention, chromosomal DNA prepared from Rhizobium sp. MCI2643 described above, is used to prepare a phagemide library by a known routine method. According to the method by Saito, et al. (Proc. Natl. Acad. Sci. USA, 83, 8664–8668, 1986), phagemides from the DNA library are transformed into host cells which are then to be cultured. By the colony hybridization method (Molecular Cloning, Cold Spring Harbor Laboratory, 320–328, 1982), colonies formed through the culture are selected using, as a probe, a partial DNA fragment or a DNA fragment having a nucleotide sequence corresponding to a part of the identified amino acid sequence of the protein, to generate the objective DNA.

The probe to be used for the colony hybridization method is a DNA fragment of a part of the gene encoding the AM24 protein generated by the polymerase chain reaction (abbreviated as "PCR" hereinafter) (Science, 239, 487–491, 1982. By effecting PCR using the +- chain DNA primer of SEQ ID No. 7 (corresponding to the amino acids from No. 1 to No. 7 of amino acid sequence of SEQ ID No. 1) and the-chain DNA primer of SEQ ID No. 8 (corresponding to the amino acids from No. 2 to No. 9 of amino acid sequence of SEQ ID No. 3 or the amino acids from No. 3 to No. 9 of amino acid sequence of SEQ ID No. 4), the resulting 966-bp DNA fragment shown in SEQ ID No. 5 is used as the probe. Use may be made of an oligonucleotide synthesized on the basis of the DNA sequence deduced from the amino acid sequence of the AM24 protein.

By the method of T. Maniatis et al. (Molecular Cloning, Cold Spring Harbor Laboratory, 85, 1982), the positive colonies in the above screening may be used to prepare DNA, which is cleaved with an appropriate restriction enzyme, for example, BamHI, and is then cloned into a plasmid such as pUC18. Then, the nucleotide sequence of the objective DNA fragment can be determined by the dideoxy chain termination method of Sanger et al. (Proc. Natl. Acad. Sci., USA, 74, 5463, 1977).

The thus determined nucleotide sequence of the DNA fragment (for example, SEQ ID Nos. 5 and 6) encodes the three proteins, namely, α-subunit (198 amino acid residues), β-subunit (104 amino acid residues) and γ-subunit (115 or 116 amino acid residues), containing the nucleotide sequences corresponding to a partial amino acid sequence (the amino acids from No. 1 to No. 7 of amino acid sequence of SEQ ID No. 1) of the α subunit of the purified AM24 protein shown in SEQ ID No. 1 and to a partial amino acid sequence (the amino acids from No. 2 to No. 8 of amino acid sequence of SEQ ID No. 3 or the amino acids from No. 3 to No. 9 of amino acid sequence of SEQ ID No. 4) of the γ-subunit of the purified AM24 protein shown in SEQ ID No. 3 or 4 and being composed of 594, 312 and 345 or 348 nucleotides, individually. The DNA fragment of the present invention is not limited to the one encoding the amino acid sequences of SEQ ID Nos. 1 to 4, but includes the one encoding the modifications of the amino acid sequences as long as the fragment has the hydration activity to convert a nitrile to an amide.

The DNA fragment thus obtained is modified at its 5' terminus and is subsequently inserted into a known expression vector downstream the promoter by a known method, and the expression vector with the DNA inserted is introduced into a known host cell such as Escherichia coli, yeast, animal cells, etc., by a known method.

The method for preparing the AM24 protein of the present invention will now be explained in detail. As an expression vector, use is made of an expression vector containing a promoter at a site where the DNA encoding the AM24 protein obtained in the above described method can be transcribed. If a host is a microorganism such as Escherichia coli and Bacillus subtilis, an expression vector preferably comprises a promoter, a Shine-Dalgarno (SD) sequence, the gene of the AM24 protein, a transcription termination sequence, and a promoter regulating gene.

The promoter includes those derived from Eschericia coli, phages, etc., for example, tryptophan synthase (trp), lactose operon (lac), lambda phage $P_L$, $P_R$, and P25 and P26 promoters which are the promoters of the initial genes of T5, and the like. The promoter may be an independently modified and designed promoter, for example, pac promoter (Agric. Biol. Chem., 52, 983–88, 1988).

The Shine-Dalgarno sequences may be those derived from Escherichia coli, phages, etc., or may be those having a consensus sequence having over a region of 4 or more continuous bases a complimentary sequence to the 3' terminal region of 16S ribosome RNA generated by DNA synthesis.

The transcription termination sequence may not be necessary, but preference is given to those containing ρ-independent sequences such as those of lipoprotein terminator, trp operon terminator, etc.

Furthermore, the order of the elements required for such expression on an expression plasmid is preferably a promoter, the SD sequence, the gene of the AM24 protein and a transcription termination element, in this order, from 5' upstream.

Also, use can be made of a process comprising increasing the copy number of the transcription unit on the vector by inserting a plurality of the unit of the SD sequence and the gene of the AM24 protein on the expression vector in an identical direction (Japanese Patent Application Laid-open No. 95795/1989).

The expression vector to be used includes pUAI2 (Japanese Patent Application Laid-open No. 95798/1989) and pKK 233-2 commercially available (manufactured by Pharmacia), and the like. Additionally, pGEX series, expression vectors capable of producing a fused protein, may be used as well.

The process of transforming hosts may follow a routine method.

The transformant may be cultured according to the method described in Molecular Cloning, Cold Spring Harbor Laboratory, 1982. The temperature for culture may appropriately be 28° to 42° C.

The host to be used for transcription may be *Escherichia coli*, as described in the working examples below, but the host is not specifically limited to *Escherichia coli*. Host organisms such as other microorganisms, animal cells and insect cells, may be used as well.

The AM24 protein obtained by culturing the transformant is isolated and purified from a host by a known method.

For the conversion from nitriles to amides of the present invention, use may be made of the culture broth of the transformant, the microorganism isolated from the culture broth, the treated microorganism, the immobilized microorganism, the crude enzyme solutions, the treated enzymes, the immobilized enzymes and the like.

The nitrile of the present invention includes, for example, nitrile having 2 to 4 carbon atoms such as acetonitrile, propionitrile, acrylonitrile, methacrylonitrile, n-butyronitrile, isobutyronitrile and the like. Acrylonitrile is representative.

The present invention will now be explained in more detail in the following working examples, but unless departing from the spirit and scope of the invention, the invention is not limited to the examples.

EXAMPLE 1

Purification of AM24 protein and determination of a partial amino acid sequence

A bacterium isolated from soil, Rhizobium sp. MCI2643 was cultured in a culture medium (20 g/l glucose, 7.5 g/l urea, 0.5 g/l $K_2HPO_4$, 0.5 g/l $KH_2PO_4$, 0.5 g/l $MgSO_4.7H_2O$, 10 mg/l $CoCl_2.6H_2O$, 1 g/l yeast extract, 5 g/l polypeptone) at 28° C. for 40 hours, followed by centrifugation (6,000×g, 20 minutes) for harvest. The harvested bacteria were washed in physiological saline and were suspended again in a buffer (50 mM HEPES/NaOH, 0.1M NaCl, pH 8.0). The suspension was sonicated (100 W, 10 minutes) under ice cooling, followed by centrifugation at 25,000×g for 20 minutes to recover the supernatant. Adding gradually to the supernatant saturated ammonium sulfate to a final concentration of 25% (w/v), the resulting precipitate was centrifuged at 25,000×g for 20 minutes and discarded. Adding to the supernatant saturated ammonium sulfate to a final concentration of 65% (w/v), the resulting precipitate was centrifuged at 25,000×g for 20 minutes and collected. The precipitate was dissolved in the aforementioned buffer at 4° C., followed by addition of saturated ammonium sulfate to a final concentration of 25% (w/v). The resulting solution was then fractionated on a Butyl-Toyopearl column (1.2×20 cm). That is, the column was thoroughly washed with a buffer containing 25% ammonium sulfate, followed by 25% to 0% (w/v) ammonium sulfate gradient elution to collect the fraction having the nitrile hydratase activity.

The active fraction was dialyzed against 10 mM bis-tris-propane, pH 6.5, and then applied to a DEAE-Toyopearl column (0.7×20 cm) equilibrated with the same solution. Washing the column with the same solution, 0 to 0.7M NaCl gradient elution was done to fractionate an active fraction. The fraction was concentrated using Ultra free (10,000 cut-off) manufactured by Millipore, and subsequently applied to a TSK gel G3000SW column equilibrated with a buffer (50 mM HEPES/NaOH, 0.1M NaCl, pH 7.5). After column washing, 0 to 0.7M NaCl gradient elution was effected. Among the fractions, the main peak eluted at volume 13.5 ml exhibited the nitrile hydratase activity, which was a single band by electrophoresis under a non-reductive condition.

Furthermore, the fraction was applied to a YMC pack C4 column (AP-802 S-5 300A C4, 0.46×15 cm) equilibrated with 20% acetonitrile containing 0.1% TFA (trifluoroacetic acid), followed by gradient elution from 20% to 60% acetonitrile to separate three types of subunit fractions. These fractions were individually dried under reduced pressure, dissolved in 60 μl of 50% TFA, adsorbed onto a glass filter treated with polybrene, and subjected to Edman degradation with a sequencer of Type 477 manufactured by Applied Biosystems to determine the amino acid sequence from the N-terminus. Among the purified subunits, β-subunit was dissolved in 50 mM Tris-HCl buffer, pH 8.5, and reacted with lysyl endopeptidase manufactured by WAKO Chemicals at a ratio of enzyme to substrate of 1:200° at 37° C. for 18 hours, which was then subjected to high-performance liquid chromatography (HPLC) to yield peptide fragments. The amino acid sequence of one of the peptide fragments was also determined. Consequently, it was indicated that the amino acid sequence of the N-terminus of α-subunit was SEQ ID No. 9; the amino acid sequence of the N-terminus of β-subunit was SEQ ID No. 10; the amino acid sequence of the lysyl endopeptidase fragment of β-subunit was SEQ ID No. 11; and the amino acid sequence of the N-terminus of γ-subunit was SEQ ID No. 12.

Further, the analysis of the purified AM24 protein by 15% SDS polyacrylamide gel electrophoresis indicated that the molecular weights of the individual subunits, namely α-subunit, β-subunit and γ-subunit, were 26,000±500 Dalton, 15,000±500 Dalton, and 16,500±500 Dalton, respetively.

Still further, the amino acid sequences of the α-subunit, β-subunit and γ-subunit of the AM24 protein were as shown in SEQ ID Nos. 1, 2, 3 or 4, respectively.

EXAMPLE 2

Evaluation of the nitrile hydratase acvity of AM24 protein (1)

The activities of the separated bacterium and enzyme solution (solution of the AM24 protein) were determined as follows. One volume of 7% (v/v) acrylonitrile and 3 volumes of 0.1M phosphate buffer, pH 7.0, were added to 1 volume of the bacterial suspension or the enzyme solution and reacted together at 25° C. for 10 minutes. After the reaction, 1 volume of 1N HCl was added to terminate the reaction, followed by 100-fold dilution with pure water. The resulting diluted solution (10 μl) was applied to an ODS column (Nuceosil 100-5C18) for HPLC, which was then eluted with 0.1M sodium dihydrogenphosphate solution containing 10% acetonitrile. The product acrylamide was immediately detected by photospectrometry at λ=195 nm.

EXAMPLE 3

Evaluation of the nitrile hydratase activity of AM24 protein (2)

One volume of the AM24 protein solution (its absorbance was 0.1 at 280 nm) and 4 volumes of 0.5M phosphate buffer, pH 7.0 were mixed together, to which were added 90 volumes of a 0.2% (v/v) solution of a nitrile compound for reaction at 25° C. for 5 minutes. After the reaction, 5 volumes of 1N HCl were added to terminate the reaction, and the resulting solution was then applied to an ODS column for HPLC, to measure the resulting amide compound. As the nitrile compound as the substrate, use was made of acrylonitrile, propionitrile, n-butyronitrile, isobutyronitrile, acetonitrile, chloroacetonitrile, malonamidenitrile, methacrylonitrile, 3-cyanopyridine, benzonitrile, and chrotononitrile.

The relative activity of each substrate is shown in Table 1, provided that the activity is defined as 100 when acrylonitrile is used as a reaction substrate.

Thus, it is indicated that the AM24 protein of the present invention can be used for producing from a variety of nitriles the corresponding amides.

TABLE 1

| Substrate Specificity of AM24 Protein | |
|---|---|
| Substrate | Specific activity (%) |
| Acrylonitrile | 100 |
| Propionitrile | 59 |
| n-Butyronitrile | 152 |
| Isobutyronitrile | 28 |
| Acetonitrile | 47 |
| Chloroacetonitrile | 671 |
| Malonamidenitrile | 143 |
| Methacrylonitrile | 143 |
| 3-Cyanopyridine | 9 |
| Benzonitrile | 251 |
| Chrotononitrile | 34 |

EXAMPLE 4

Preparation of a partial DNA fragment AM24 protein by PCR

The chromosomal DNA of a substrate bacterium separated from soil, namely Rhizobium sp. MCI2643 (as described above), can be prepared by a routine method. That is, the DNA was prepared from the cultured bacterium, by slight modification of the phenol-chloroform method (Molecular Cloning, Cold Spring Harbor Laboratory, 1982) as follows.

Strain Rhizobium sp. MCI2643 was inoculated and cultured in 100 ml of the culture medium of the Example 1, and were then harvested. The strain were washed in TES (10 mM Tris-HCl, pH 7.5, 1 mM EDTA, 50 mM NaCl), and suspended in 5 ml of TE (10 mM Tris-HCl, pH 7.5, 1 mM EDTA), followed by addition of 10 mg of lysozyme for incubation at 37° C. for 30 minutes. Through subsequent repetition of lyophilization and reconstitution, the cells were disrupted.

Then, 1% (w/v) SDS was gradually added under stirring to a final concentration of 0.33%, followed by further addition of proteinase K (manufactured by Sigma, Co. Ltd.) to a final concentration of 0.1 mg/ml. The resulting mixture was then incubated at 60° C. for 5 hours. An equal volume of TE saturated phenl-chloroform was added and gently shaken at room temperature overnight (this procedure was referred to as "phenol treatment" hereinbelow). After centrifugation, the upper phase was collected, to which was then added an equal volume of chloroform for re-extraction. After adding an equal volume of ethanol to the upper phase after centrifugation, DNA was wound and taken out with a glass bar, and was subsequently dehydrated with 70%, 85% and 99.5% ethanol, sequentially. Then, the DNA was dissolved in 3 ml of TE buffer, followed by addition of an aqueous DNase free RNase A solution to a final concentration of 10 μg/ml and incubation at 37° C. for 1 hour. Subsequently, the DNA was recovered through phenol treatment and ethanol precipitation. Consequently, 700 μg of the chromosomal DNA was obtained.

PCR was carried out using a Perkin Elmer Cetus DNA Thermal Cycler together with Gene AMP DNA Amplification Reagent Kit (manufactured by TAKARA LIQUOR) according to the manufacturer's instruction. That is, a 100 μl solution was prepared by mixing 1 μl (an amount corresponding to 0.5 μg) of a substrate DNA, 10 μl of a 10-fold concentration of a reaction buffer (500 mM KCl, 100 mM Tris-HCl, pH 8.3, 15 mM MgCl$_2$, and 0.% (w/v) gelatin), 16 μl of 1.25 mM 4dNTP, 5 μl each of 50 μM primer #1 of the + chain DNA primer 5'ATGGAA/GCCNTAC/TAC-NAAA/GCC3' (20 nucleotides, "N" means "inosine", SEQ ID No. 7) corresponding to the amino acids from No. 1 to No. 7 of amino acid sequence of SEQ ID No. 1 and primer #2 of the − chain DNA primer 5'A-TA/GTCC/TTCIGGA/GTTIACICC3' (20 nucleotides, SEQ ID No. 8) corresponding to the amino acids from No. 2 to No. 9 of amino acid sequence of SEQ ID No. 3 or the amino acids from No. 3 to No. 9 of amino acid sequence of SEQ ID No. 4 and 0.5 μl of Taq DNA polymerase.

The reaction was carried out as follows; 35 cycles were repeated, each cycle being composed of pretreatment at 94° C. for 10 minutes and subsequent incubation at 94° C. for 1 minute (modification stage), incubation at 46° C. for 1.5 minutes (annealing stage) and incubation at 72° C. for 2 minutes (elongation stage) The reaction was terminated after the final incubation at 72° C. for 7 minutes. The resulting reaction solution was extracted with phenol:chloroform=1:1, followed by ethanol precipitation. The precipitate was dissolved in 16 μl of sterile deionized water, followed by 5% polyacrylamide gel electrophoresis, and the 966-bp band was recovered according to a routine method followed by ethanol precipitation. The DNA precipitate was dissolved in 16 μl of sterile deionized water, followed by addition of 2 μl of a 10-fold concetration of T4 DNA polymerase buffer (0.33M Tris-acetate, PH 7.9, 0.66M potassium acetate, 0.1M magnesium acetate, 5 mM DTT), 1 μl of 1.25 mM 4dNTP, and 1 μl of T4 DNA polymerase (6 units) to prepare a solution of 20 μl in total, which was then subjected to reaction at 37° C. for 30 minutes. Thus, double-stranded, blunt ended DNA was collected.

After the DNA fragment was inserted into the SmaI site of UC118 vector, the nucleotide sequence thereof was determined with a fluoroscopic DNA sequencer manufactured by Dupont. The nucleotide sequence of the PCR fragment was determined as shown in SEQ ID No. 5. In the amino acid sequence encoded by the 966-bp DNA fragment, 40 amino acid residues from the 5' terminus corresponded to the amino acids from No. 1 to No. 40 of amino acid sequence of SEQ ID No. 1; 7 amino acid residues from the 3' terminus corresponded to the amino acids from No. 2 to No. 7 of amino acid sequence of SEQ ID No. 3; and 8 amino acid residues from the 3' terminus corresponded to the amino acids from No. 1 to No. 8 of amino acid sequence of SEQ ID No. 4. Thus, the amino acid sequence completely coincided with the amino acid sequence determined from the purified AM24 protein.

EXAMPLE 5

Screening of a clone containing the DNA fragment encoding the AM24 protein in full length The 966-bp PCR fragment prepared in the above Example 4 was labeled with $^{32}P$ according to the method described in Molecular Cloning, Cold Spring Harbor Laboratory, 1982, which was then used as a probe for screening.

To 10 μl (an amount corresponding to 5 μg) of the chromosomal DNA sample prepared in the above Example 4 was added 3 μl of a 10-fold concentrated restriction enzyme buffer (500 mM Tris-HCl, pH 7.5, 100 mM magnesium chloride, 1M sodium chloride, 10 mM DTT), 16 μl of sterile deionized water, and 1 μl (15 units) of restriction enzyme BglII for reaction at 37° C. for 2 hours, followed by agarose gel electrophoresis (65 V, 4 hours) and Southern hybridization using the probe described above according to Molecular Cloning (Cold Spring Harbor Laboratory, 1982). Consequently, it was indicated that a DNA fragment capable of strongly hybridizing with the probe was present at a position of about 5.2 Kb.

Then, to 40 μl (an amount corresponding to 20 μg) of the chromosomal DNA sample were added 8 μl of a 10-fold concentrated restriction enzyme buffer (500 mM Tris-HCl, pH 7.5, 100 mM magnesium chloride, 1M sodium chloride, 10 mM DTT), 29 μl of sterile deionized water, and 3 μl (45 unit) of restriction enzyme BglII for reaction at 37° C. for 2 hours, followed by subsequent agarose gel electrophoresis (65 V, 5 hours) to separate and recover DNA fragments of about 5.2 Kb according to the method described in Molecular Cloning (Cold Spring Harbor Laboratory, 1982).

The DNA fragment of about 5.2 Kb thus recovered was prepared in an amount of at least 10 pmole, which was then inserted into the BamHI site within the multicloning site of the Charomide 9-36 cloning vector (manufactured by Nippon Gene, Co. Ltd.) using a ligation kit (manufactured by TAKARA LIQUOR). 1 μg of the vector DNA prepared as follows was used for such ligation. The Charomide 9-36 cloning vector was cleaved with the restriction enzyme BamHI (manufactured b TOYOBO, Co. Ltd.) followed by phenol/chloroform treatment and ethanol precipitation and subsequent 5' terminal dephosphorylation with alkaline phosphatase (manufactured by BOEHRINGER MANNHEIM, Co. Ltd.) (Molecular Cloning, Cold Spring Harbor Laboratory, 1982), further followed by phenol-chloroform treatment and ethanol precipitation.

The thus prepared DNA was packaged into λ-phage particles using the Giga Pack Gold Packaging Kit manufactured by STRATAGENE. According to the manufacturer's instruction enclosed in the kit, 2 μl of a solution of the ligated DNA was used for reaction. After the packaging reaction, transfection was done following the enclosed manufacturer's instruction. The serially diluted bacterial solution was coated onto an Ampicillin (50 μg/ml) containing LB agar mediu (1% yeast extract, 0.5% Bactotryptone, 0.5% sodium chloride) in a petri dish of a 15-cm diameter. Petri dishes with $10^2$ to $10^3$ colonies per dish were used for bank screening. E. coli 5α competent cells (COMPETENT HIGH) manufactured by TOYOBO, CO. LTD. were used for transfection.

Following the enclosed instructions, bank screening was done using a nylon membrane, i.e. Colony/Plaque Screen manufactured by NEN, Co. Ltd. That is, the colonies cultured on one plate were transferred onto two membranes, which were left to stand on filter papers immersed with 0.1M sodium hydroxide and 0.5M sodium chloride for 2 minutes, and were further left to stand alone on filters immersed with 1.5M sodium chloride-0.5M Tris-HCl, pH 7.5, for 5 minutes. After further repeating such treatment with filters two times, the filters were washed in 2×SSC (two-fold SSC solution) and air dried on dry filter papers. Then, the DNA transferred onto the membranes was immobilized by UV irradiation at 120 mJ/cm$^2$.

The four membranes (corresponding to 5,000 colonies) thus treated were impregnated with 15 ml of a hybridization solution [3×SSC, 0.1% SDS, 10×Denhardt (a 10-fold concentration of Denhardt; 1% bovine serum albumin, 1% polyvinylpyrrolidone, 1% Ficoll 400), 10 μg/ml salmon sperm DNA] at 65° C. for 2 hours. During that time, the 966-bp DNA fragment prepared in Example 4 was labeled with $^{32}P$ using the PCR primer #2 described in Example 4, according to the usual method. The aforementioned filters were impregnated with 15 ml of a fresh hybridization solution containing the $^{32}P$-labeled DNA fragment at a level of 1μ Ci/ml at 65° C. for 20 hours. Then, the membranes were taken out and washed twice in a 2×SSC solution containing 1% SDS, and further washed twice in a 0.2×SSC solution containing 0.1% SDS at 65° C. for 15 minutes, followed by autoradiography. Consequently, a colony was identified, where positive signals on the autoradiograms of a pair of membranes agreed well with each other.

The colony was cultured in an LB culture medium (1% yeast extract, 0.5% Bactopeptone, 0.5% sodium chloride) and subsequently diluted. About 100 colonies were inoculated onto an LB agar medium (containing 50 μg/ml Ampicillin) per dish, followed again by the hybridization using the $^{32}P$-labeled DNA fragment to identify positive single colony clones.

EXAMPLE 6

Subcloning of the DNA fragment and detmination of its nucleotide sequence

From the identified clones, plasmid DNA was prepared according to the usual method (Molecular Cloning, Cold Spring Harbor Laboratory, 86–89 (1982)), from which the DNA region required was then appropriately cleaved into small fragments with restriction enzymes. The fragments were then subcloned into plasmid vectors pUC18 and pUC19. From the resulting subclones, plasmid DNA was prepared according to the usual method, and its sequence was determined using a fluoroscopic sequencer, GENESIS 2000 System manufactured by Dupont. As the sequence primers, use was made of the following two types of synthetic primers; 5'd(GTAAAACGACGGCCAGT)3' (SEQ ID No. 13) and 5'd(CAGGAAACAGCTATGAC)3' (SEQ ID No. 14) to determine the nucleotide sequences of the +- chain and −chain of the DNA fragments. Consequently, the nucleotide sequence shown in SEQ ID No.

5 was obtained. Thus, a DNA fragment of 5.2 Kb in full length, containing the region encoding the amino acid sequence identified in Examples 1 and 4 was cloned and its nucleotide sequence was determined.

EXAMPLE 7

Construction of a plasmid producing AM24 protein and obtainment of a transformant Charomide pChAM24-1 (FIG. 1) containing the DNA of the AM24 protein gene produced in Example 6 was prepared according to the usual method. After digesting 2 μg of the plasmid DNA with restriction enzyme XbaI, the DNA terminus was blunt ended with T4 DNA polymerase. After separating the DNA fragment containing the objective AM24 protein encoding region by polyacrylamide gel electrophoresis followed by phenol/chloroform extraction, the DNA fragment was purified through ethanol precipitation and then dissolved in 10 μl of sterile water. Subsequently, 1 μl of this solution was mixed with 10 ng of the expression vector pUSI2 (Japanese Patent Application Laid-open No. 95798/1989) which was cleaved with the restriction enzymeSmaI, and dephosphorylated using alkaline phosphatase from calf intestinal mucosa, and the two were ligated together using a DNA ligation kit (manufactured by TAKARA LIQUOR).

Using the reaction solution, Escherichia coli DH5 α cells were transformed and analyzed by the method of Maniatis et al. (Molecular Cloning, 365-381 (1982)), thereby obtaining a transformant including an AM24 protein expression plasmid, pEAM24X1 (FIG. 2) with the DNA fragment inserted in the same direction as the transcription direction of the promoter of the expression vector.

EXAMPLE 8

Expression of AM24 protein using a transformant and conversion of a nitrile into an amide The transformant containing the pEAM24X1 obtained in Example 7 was cultured overnight at 27° C. in 10 ml of an LB culture medium (containing 50 μg/ml Ampicillin). One hundredth in volume of the culture broth was added to and cultured in 10 ml of an LB medium (containing 50 μg/ml Ampicillin, 10 μg/ml $CoCl_2.5H_2O$) at 27° C. for 2 hours, and then, IPTG was added as a transcriptional inducer to a final concentration of 1 mM, followed by further culturing at 27° C. for 12 hours. The strain were centrifuged and harvested, washed once in physiological saline, and suspended in 1.6 ml of a phosphate buffer (pH 7.0, 0.1M). 0.32 ml of the suspension was sampled, followed by mixing with 80 μl of an aqueous 7% acrylonitrile solution for reaction at 30° C. for 1 hour. After the termination of the reaction by addition of HCl as described before, the acrylamide and acrylonitrile concentrations in the reaction solution were determined by HPLC. Thus the conversion of acrylonitrile to acrylamide was found to be complete.

On the contrary, no acrylamide was detected in the reaction solution after the termination of the reaction when Escherichia coli DH5 α cells lacking the expression plasmid, pEAM24X1 was used.

When the transformant harboring pEAM24X1 was cultured in a culture medium without cobalt, no acrylamide was detected in the reaction solution after the termination of the reaction. Thus cobalt is essential for nitrile hydratase activity.

EXAMPLE 9

Purification of AM24 protein from the transformant and determination of a partial amino acid sequence After washing 0.9 g in wet cell weight of the transformant cultured by the method of Example 8 in physiological saline, the washed transformant was suspended in a buffer (50 mM HEPES/NaOH, 0.1M NaCl, pH 8.0). The suspension was sonicated (100 W, 5 minutes) under ice cooling, followed by centrifugation at 25,000× g for 20 minutes to recover the supernatant. The supernatant was purified sequentially with ammonium sulfate fractionation, Butyl-Toyopearl column chromatography, DEAE-Toyopearl column chromatography, and TSK gel G3000SW column chromatography, as in Example 1. Thus, a purified product of a single band on polyacrylamide gel electrophoresis was produced. The purified product had the equal molecular weight and specific activity as those of the AM24 protein purified from Rhizobium sp. MCI2643 strain.

The purified product was fragmented with lysyl endopeptidase in the same manner as in Example 1, and partial amino acid sequences of two fragments were determined. The amino acid sequences of the individual peptide fragments were the same as partial amino acid sequences (SEQ ID No. 1 and No. 3 or 4) of the amino acid sequence of the AM24 protein, which were deduced from SEQ ID No. 5.

In accordance with the present invention, a novel DNA fragment encoding the polypeptide having the amino acid sequences of the three subunits, α, β and γ subunits, and also showing nitrile hydratase activity, was obtained. Additionally, the nucleotide sequence thereof was also determined. By the use of the microorganism and the microorganism extract and the like obtained by culturing the transformant harboring the expression plasmid constructed of the present invention, nitrile compounds can be converted into the corresponding amide compounds. The present invention can be used for efficiently producing amides from nitriles.

---

What is claimed is:

1. An isolated and purified protein from Rhizobium sp. MCI2643 characterized by having the following physico-chemical properties:
   i. a water-soluble enzyme composed of three subunits and having a molecular weight of about 110,000 determined by gel filtration, wherein the molecular weights of the subunits determined by SDS-polyacrylamide gel electrophoresis are as follows:
      (a) molecular weight of subunit $\alpha$; 26,000±500 Dalton
      (b) molecular weight of subunit $\beta$; 15,000±500 Dalton
      (c) molecular weight of subunit $\gamma$; 16,500±500 Dalton; and
   ii. having nitrile hydratase activity.

2. A protein according to claim 1, wherein the subunit $\alpha$ is represented by the amino acid sequence of SEQ ID No. 1.

3. A protein according to claim 1, wherein the subunit $\beta$ is represented by the amino acid sequence of SEQ ID No. 2.

4. A protein according to claim 1, wherein the subunit $\gamma$ is represented by the amino acid sequence of SEQ ID No. 3 or 4.